Oct. 21, 1969 S. CALVINO Plant Pat. 2,933
HYBRID TEA ROSE PLANT, SPECIALLY ADAPTED FOR LARGE-SCALE CULTIVATION FOR CUT FLOWER PRODUCTION
Filed Nov. 21, 1967
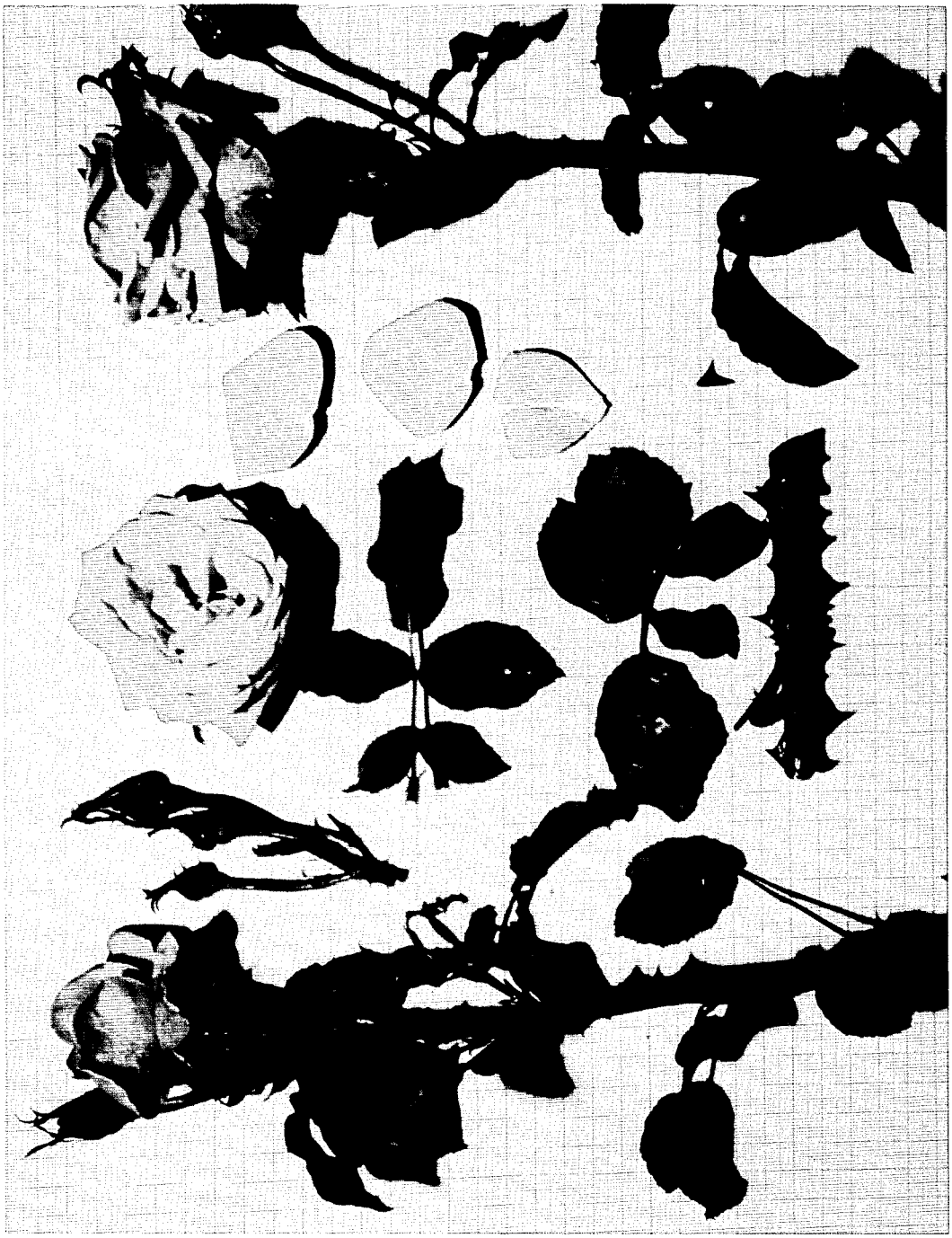

United States Patent Office

Plant Pat. 2,933
Patented Oct. 21, 1969

2,933

HYBRID TEA ROSE PLANT, SPECIALLY ADAPTED FOR LARGE-SCALE CULTIVATION FOR CUT FLOWER PRODUCTION

Stefano Calvino, Strada Coldirodi 65, San Remo, Italy

Filed Nov. 21, 1967, Ser. No. 684,878
Int. Cl. A01h 5/02
U.S. Cl. Plt.—20 1 Claim The present invention relates to a new hybrid tea rose plant, specially adapted for large-scale cultivation for cut flower production in the open air as well as in greenhouses.

The rose of this invention has been produced by the applicant after several years of extensive research by means of the genetic cross-breeding of different varieties appropriately chosen so as to bring together the desired characteristics in the same plant and create a type of flower meeting the wishes of international flower consumers. The new type of plant had to satisfy the following requirements: (a) The flowers had to be of medium to large size, sufficiently large to provide a color patch in floral compositions but not so large as to become too heavy for export. The color of the flowers had to be included in the medium intensity range of red, brilliant under artificial light yet withstanding discoloration by sunlight and inclement weather, with a special shade appreciated on the market. (b) The flower stems had to be sufficiently long, rigid and straight and had to bear the flower gracefully and harmoniously, with a slender, erect, straight peduncle. (c) The flowers had to bloom easily, even after they had been cut; be resistant to packaging and long-distance shipment after having been cut. (d) The plant should grow vigorously and sprout when grafted on any type of recipient usually employed in large-scale cultivation, recover promptly after pruning and have a greater productivity than normal varieties previously cultivated. (e) The leaves, sufficiently abundant and decorative, had to be particularly resistant to fungus attack generally affecting roses in large-scale cultivation.

Thus a new variety of rose for large-scale cultivation had to be developed, having improved characteristics regarding the quality of the flower and its acceptability by the public at large, as well as the properties of the plant, so as to render its cultivation much more profitable in comparison with other varieties of the same class.

The applicant therefore carried out a thorough research and made numerous atempts which finally led to positive and satisfactory results. Starting in fact from a numerous stock of hybrid varieties produced by fecundation of a previously unknown hybrid variety bearing red flowers with polyantha roses known as "Ninfa Rossa" variety, it was possible to isolate or select the plant which is the subject of this invention, and finally meet the targets of this research. The rose Ninfa Rossa is a sport (lusus naturae) of the variety Nymph obtained by A. Dickson in 1953—rose flowered, with salmon-coral colored flowers, which has changed the colors of its flowers in red. The parentage of the new rose is an unnamed seedling, red flowered × "Ninfa Rossa."

The variety which is the subject of this invention is in fact excellently adapted for the large-scale production of flowers to be cut, and represents a considerable improvement on other varieties of the same class.

The variety in accordance with this invention can easily be reproduced in any number of specimens, all of them having the properties of the original plant, by means of one of the development methods for plants commonly used in flower cultivation, specifically by taking from the original plant or a plant deriving from it a bud and grafting the later by known techniques on a different species of rose (the graft recipient) adapted to the soil in which the variety is to be cultivated. It will thus be possible to obtain fully developed plants suitable for producing cut flowers on an industrial or commercial scale, with all the distinctive properties of the original plant.

These properties are listed, by way of example and without any limitations, in the following description based on a set of plants cultivated according to industrial criteria in the open air and in full soil on a sunny hillside at San Remo in the month of September.

Reference should always be made to these climatic and seasonal conditions with regard to the purchase of the plant in the light of the present description. Any differences which, as a result of different conditions of climate, soil or method of cultivation, may be encountered between certain features of the plant and the corresponding ones of the description must be considered normal and do not modify the essence of the present invention, as least so long as it is possible to identify the plant by means of the collection of features given in the description by repeating the cultivation under the same conditions as those of the plants described.

In the description the colors have been named according to the tables of the "Horticultural Color Chart" by Robert F. Wilson (indicated in the text by the initials HCC) except in those cases in which the colors were absent from the tables or where its indication is sufficiently clear according to common parlance.

Classification: Hybrid tea.

Stock: "Unknown hybrid with red flowers" × "Ninfa Rossa" polyantha with red flowers (see identification supra).

PLANT

Growth: Bushy, with vertical erect growth of average compactness, leaves abundant.

Average height: 140–170 cm. from the ground at the apex of the stems for 2–3 year plants grafted on *Rosa indica major*.

Roots: Fairly developed; development variable according to the type of graft recipient used. On *Rosa indica major* they are fairly numerous starting from the collar, ramified with sparse root hairs. On average 4–6, average length 40–60 cm., average diameter at the collar 5–12 mm., color dark brown.

Stem: Varying according to the type of graft recipient used for the propagation. Generally consisting of the recipient itself. In plants grafted on *Rosa indica major* it is on average 25–30 cm. long with a 12–16 mm. diameter at the collar, cylindrical, sometimes slightly thicker towards the top. Globular grafting point. Bark lavender green tinted in dark brown in its lower part.

Main branches: Varying in number and shape according to the system adopted for pruning; generally strong, fairly numerous, ascending, from 4 to 6 on average, starting from the grafting point and from the stem at short intervals, inserted sometimes in the base of other branches, slightly divergent from the axis of the plant, articulated in slender internodes 40–70 mm. on average, of varying length without any definite rule, strong and fairly differentiated nodes.

*Size.*—Varying according to the method of pruning. Average length, 30–50 cm.; average diameter at the base, 8–15 mm.

*Bark.*—Smooth hairless, slightly rough lengthwise of the base of the main branches; average thickness.

*Thorns.*—Fairly or very numerous, variable sizes, with very small thorns intermixed with large ones and very large ones, singly inserted on the branch, seldom budding, difficult to detach from the bark. Shape—triangular with slightly curved sides and lower side concave. Sharp and fairly differentiated tip slightly tilted downwards and straight. Oval, fairly broadened base. Size: Large thorns—average length 9–12 mm.; average breadth 10–14 mm.; average thickness 3–5 mm. Small thorns—average length 0.5–1 mm.; average breadth 1–2 mm.; thickness 0.5–1 mm. Color—chamois tinted with brown at the tip. Consistency—hard and woody.

Flower stems: On average from 2 to 4 on each main branch, preferably inserted in the higher part of the latter.

*Shape.*—Approximately cylindrical; diameter gradually decreasing upwards, slender, erect, rigid, straight or slightly sinuous, articulated in numerous elongated internodes, on average from 40 to 70 mm. long, with fairly differentiated nodes. Flower peduncle differentiated, with short tender needle-shaped thorns, average length 80–120 mm., average diameter 3–5 mm., rigid, erect, slightly sinuous.

*Size.*—Average length of stems 70–110 cm.; average diameter at base 5–10 mm.

*Color.*—Spinach green background (HCC, page 187, shade 60–60/1), occasionally covered lengthwise by grenade brown color (HCC, page 192, shades 18/1.2). The same color is more widely found on the young vegetation and on the apical shoots of the flower stems.

*Bark.*—Smoth, hairless, slightly pruinose, opaque or slightly satiny, average thickness.

*Large thorns.*—Fairly numerous, scattered on stems, on average from 2 to 4 per internode intermingled with many small needle-shaped thorns. Shape—triangular with upper side almost straight and lower side concave, sharp, straight or slightly hooked tip. Size: Large thorns—average length 6–9 mm., average breadth 8–12 mm., average thickness 2–4 mm. Small thorns—average length 0–1 mm., average breadth 1–2 mm., thickness 0.5–1 mm. Color—greenish yellow tinted at the point with violet purple (HCC, page 177, shades 28/2.3). Consistency—semi-woody, resistant.

*Small thorns.*—Numerous and scattered, triangular with a narrow oval base, straight tip, easily detachable from bark. Average size—length 2–3 mm., breadth 3–5 mm., thickness 1 mm. or less. Color—almost violet purple (HCC, page 177, shades 28/2/3). Consistency—sub-woody, often slightly more tender.

*Leaf shape.*—Elongated, comprising 3–5–7 folioles, generally 7 in the lower part of the plant, 5 in the middle part and 3 in the upper part, inserted in opposing pairs plus a terminal foliole on a sturdy rachis, rather short, straight or slightly angled in the points where the folioles are inserted.

*Bearing.*—Scarcely or fairly diverging from the stems, sometimes horizontal or drooping in the terminal part. Peduncle short or almost sessile, often inserted on the rachis in points offset in relation to the opposite foliole, specially in the pair of folioles nearest to the base of the rachis. Folioles generally perpendicular to the rachis, flat or slightly upturned in relation to the plane of the leaf.

*Size.*—Average length, from attachment to tip of terminal foliole: 120–160 mm. on the main branches, 100–130 mm. on the flower stems. Breadth: 70–100 mm. on the main branches, 80–100 mm. on the flower stems.

*Folioles.*—Limb oval and rounded, sometimes amply spear-shaped; limb flat and slightly V-shaped on central longitudinal nervation, or undulated with outer edges curved upwards. Side and outer edge serrated, with sharp teeth of average size turned towards the top of the foliole. Small tip fairly differentiated at apex of foliole. Size—varying with the position on the stem and on the midrib, as follows. Leaves with 7 folioles (from the base of the leaf): 1st pair—average length 20–35 mm., breadth 15–25 mm. on average; 2nd pair—length 30–40 mm., breadth 25–30 mm.; 3rd pair—length 30–50 mm., breadth 30–35 mm. Terminal foliole—length 40–60 mm., breadth 30–40 mm. Leaves with 5 folioles: 1st pair—length 25–30 mm., breadth 20–30 mm.; 2nd pair—length 30–45 mm., breadth 25–35 mm. Terminal foliole—length 50–60 mm., breadth 35–45 mm., sometimes as much as 70 mm.

*Color.*—Upper face—spinach green background (HCC, page 187, shades 60/60/1) tinted here and there from grenade red (HCC, page 192, shades 18/1–2–2) to violet purple (HCC, page 177, shades 28/2–3). Lower face—nearing willow green (HCC page 199, shades 62/1–2) sometimes tinted with violet purple tones (HCC, page 177, shades 28/1–2–3).

*Suface.*—Upper face—smooth, hairless, shiny, sometimes slightly bubbly between nervations. Feathered nervations fairly concave in the limb. Lower face—smooth, hairless, opaque, with feathered nervations fairly protrusing on the limb.

*Consistency.*—Tough, rigid, or fairly herbaceous—resistant.

*Bearing.*—Axis of side folioles inclined towards the base of the foliole in the first pair from the base; then almost perpendicular to the rachides in the other pairs.

*Rachis.*—Sturdy, short or average length, semi-cylindrical, with a longitudinal furrow fairly marked in the upper face, with slightly hairy edges provided with glandular hairs. Small sturdy hooked thorns, from 2 to 4 in number, on the lower face of the rachis.

*Size.*—Average length 80–100 mm. from the attachment to the base of the terminal foliole.

*Color.*—Spinach green (HCC, page 187, shades 60/1–2–3), tinted with reddish brown at the point of attachment of the petioles. Stipulae—well differentiated, clustered on the rachis until the middle of the first internode of the latter, breadth 4–8 mm., ending in triangular ears. Edges of stipulae hairy and minutely serrated.

FLOWER

Bearing: Main flower from average to large, single at the apex of the stem, accompanied by 2 to 3 small secondary buds borne by short secondary stems inserted at the base of the flower-bearing peduncle or on the highest nodes of the stems, generally slightly longer than the main stem. Corolla: Straight along the axis of the stem.

Closed flower bud: Short oval very rounded, almost globose, with differentiated conical tip, sharp and with leafy appendices of the sepals. Early budding of sepals when petals are still completely closed.

*Size.*—Average length, 15–20 mm. at attachment of sepals. Average diameter at ⅓ of length, 14–18 mm.

Calyx: Shape—elongated urn-shaped receptacle. Sepals 5 in number, triangular and irregular, spear-shaped with very irregular dented leafy appendices; size and shape differing greatly from one sepal to another. The sepals bear on their side edges a few slender spear-shaped leafy appendices, with an average length of 5–8 mm. and breadth of 1–3 mm., with hairy serrated edges diverging from the sides of the sepals and from the closed bud. The flower peduncle is strong, straight or slightly curved, rigid with numerous short and sometimes tender needle-shaped thorns.

*Color.*—Near to spinach green (HCC, page 187, shades 60/2–3) with purple violet tones (HCC, page 177, shades 28/2–3) on one side. Surface of sepals: outer—smooth, hairless, slightly glandular; inner—downy, with a woolly down typically short, white and fine.

*Consistency.*—Average thickness, tough and fleshy.

Half-open flower bud: Urn-shaped, globose, frusto-conical tip and turbinated petals opening sideways and outwards, tangentially on the perimeter of the bud. Upper edge of petals slightly or fairly furled on the terminal margin. Outer petals slightly drooping, fairly furled on the outer margin.

*Size.*—Varying in accordance with budding stage. Average diameter, 25–40 mm.; length of flower from receptacle to apices of petals, 35–50 mm.

*Color.*—Outer of petals, from Bengal red (HCC, page 25, shades 25–25/1) to pink red (HCC, page 158, shades 21–21/1). Inner face of petals (nearly Turkish red) (HCC, page 94, shades 21–21/1).

Open corolla: From average to large, round, regular with festooned edge and a few rounded tips on the outer petals formed by their being furled up. Profile of the corolla shaped as an open hemispherical cup, the upper part being flat. Center of flower fully concave with central petals arranged dialwise or irregularly concave towards the center of the flower so that the stamens and pistils are almost covered. The outer petals are fairly furled outwardly in their terminal parts or on the side edges, so as to form tips slightly protruding on the contour of the corolla. The central petals are concave at the center, the outer margin being slightly curved outwards.

*Size.*—Average diameter in wholly open condition, 70–100 mm. Length of flower from receptacle to apex of petals, 30–50 mm. General color—from Oriental red (HCC, page 165, shades 19–19/1–2–3) to Geranium lake (HCC, page 20, shade 20) with light Turkish red tones (HCC, page 97, shades 21/2–3) at the center of the corolla.

*Petals.*—Fairly numerous, on average 35 to 50, arranged regularly in the corolla, imbricated.

*Shape.*—Outer petals—rounded limbs, concave at center, with side edges converging in the claw at angles up to 150–160°. Outer edge slightly corrugated and festooned, with frequent furls forming obtuse undefined points in the places where they meet. The claw is fairly differentiated, whitish tinted in red in the limb. Inner petals—oval, narrower and more elongated, sometimes rope-shaped, the outer edge being rounded and slightly festooned. Side edges converging in the claw at angles of 100–120°. Outer edge slightly or fairly curved outwards, not furled. A few petaloid stamens at the center of the corolla.

*Size.*—Outer petals: length, 35–45 mm.; breadth, 35-50 mm. Inner petals: length, 30–35 mm. on average; average breadth, 20–35 mm.

*Color.*—Front side of petals: Upper face from Oriental red (HCC, page 165, shades 19/19–1–2–3) to Geranium lake (HCC, page 20, shade 20) with tones in Primrose red (HCC, page 23, shades 23/2–3) around the claw. Lower face, outer part, almost Primrose red (HCC, page 23, shades 23/23–1). Claw—Aureoline yellow (HCC, page 2, shade 3/3).

*Surface.*—Upper face—satiny or slightly velvety with minute veins carved in the limb. Lower face—satiny; smooth, with minute veins upstanding from the limb.

*Consistency.*—Fairly fleshy, solid, resistant.

Organs of reproduction: Stamens—numerous, free; inserted on the receptacle around the styles. On average 100 to 120. Filaments erect, slender, yellow, straight or slightly curved; length up to 8–12 mm. Anthers long, bilocular, kidney-shaped; length 2–3 mm., breadth 0.5–2 mm. Styles are numerous, slender, glandular, in the center of the thalamus, with a thick woolly down at the base opening towards the apex. On average from 50 to 70. Trough-shaped stygmas, rosy yellow color. Ovarium almost entirely closed in the receptacle.

Scent: Slight, fruity tone.

Resistance of flowers to transport: Excellent.

Resistance of flowers to inclemency of weather: Excellent; very slight discoloration from sunlight; good resistance to wind and rain.

Resistance of plant to disease: Considerable.

Simplicity of cultivation: Excellent.

Grafting: Good sprouting power.

I claim:

1. Hybrid tea rose plant, whose first plant of this variety has been obtained through artificial fecundation of flowers of an unknown rose with red flowers with pollen from a variety called Ninfa Rossa, red-flower polyantha, characterized by:

(a) from the physical point of view: flowers from average to large size having the shape of a very graceful hemispherical cup with fairly numerous petals slightly furled outwards, color from Oriental red to Geranium lake with Turkish red shades at the center of the flower; flower stems numerous, erect and rigid, straight or slightly sinuous, abundantly covered with leaves of a color perfectly harmonized with the red color of the corolla, dark shiny green in the upper face, resistant, tough, with large thorns intermingled with smaller ones, fairly numerous and easily detachable from the bark; the plant is tall and erect, slinder, compact, the branches and stems slightly diverging from each other;

(b) from the physiological standpoint: flowers withstanding transport and inclemency of weather, hardly any discoloration from sunlight and rain, good durability after having been cut and easy to recover after long journeys; plant vigorous, not requiring delicate handling in cultivation for the large-scale production of cut flowers, withstanding inclemency of weather and fungal diseases, mildew, Oidium and black spot, considerable vegetative affinity for the main graft recipients used in large-scale cultivation.

No references cited.

ROBERT E. BAGWILL, Primary Examiner